United States Patent [19]
Gamarnik et al.

[11] Patent Number: 5,227,627
[45] Date of Patent: Jul. 13, 1993

[54] ANIMAL BODY PARTS PHANTOM

[75] Inventors: Kase M. Gamarnik; Gary H. Kramer, both of Ottawa; Léo Noel, Aylmer, all of Canada

[73] Assignee: Her Majesty in Right of Canada as represented by the Minister of Health and Welfare Canada, Ottawa, Canada

[21] Appl. No.: 729,111

[22] Filed: Jul. 16, 1991

[51] Int. Cl.$^5$ .............................................. G01D 18/00
[52] U.S. Cl. .............................. 250/252.1; 250/363.09
[58] Field of Search ................................. 378/18, 207; 250/363.09, 252.1 R, 303

[56] References Cited

U.S. PATENT DOCUMENTS

| | | | |
|---|---|---|---|
| 3,010,223 | 11/1961 | Anderson | 250/252.1 X |
| 4,472,829 | 9/1984 | Riederer et al. | 378/207 |
| 4,649,561 | 3/1987 | Arnold | 250/252.1 X |

OTHER PUBLICATIONS

Hew Publication (FDA) 76-8046, 'Quality Control for Scintillation Cameras', Jun. 1976, pp. 41-44.
Product Data, 'Phantoms for Cameras & Scanners', Jan. 1976, Atomic Development Corp.

Primary Examiner—Paul M. Dzierzynski
Assistant Examiner—Edward J. Glick
Attorney, Agent, or Firm—J. Wayne Anderson

[57] ABSTRACT

An animal body parts phantom comprised of a substrate sheet which is shaped in the form of an animal body part e.g. a thyroid, including a radioactive material substantially uniformly deposited on the substrate, and a tissue simulating material encapsulating and supporting the substrate. A container may be included to provide a mold for the tissue simulating material and to protect the phantom. An additional fat simulating overlay may also be provided to extend the capability of the device.

19 Claims, 3 Drawing Sheets

ANIMAL BODY PARTS PHANTOM

BACKGROUND OF THE INVENTION

1. Field of the Invention

The present invention relates to animal body parts calibration phantoms, and in particular to a thyroid calibration phantom for calibration of radiation detection equipment used to measure the uptake of radioactive tracer by the thyroid gland.

2. Description of the Prior Art

Conventional thyroid phantoms employ liquid solutions or dispersions of radio-iodine as the tracer material. Radio-iodine is an extremely toxic material. Accordingly, spills or leaks of such material are hazardous to the health of laboratory personnel.

One such thyroid phantom is manufactured and sold by Radiology Support Devices Inc. of Long Beach, Calif. This device comprises a hollow-shell synthetic resin material in the three-dimensional characteristic butterfly-shape of the thyroid. Posterior ports are provided for filling the device with a liquid solution/dispersion of radio-iodine or the like. A further drawback of this device is that it cannot be completely filled with the liquid. As a result an air bubble is formed which affects the accuracy of the device. Moreover, the device is made to fit snugly into a companion neck phantom which has no capacity to accept other sizes of thyroid phantoms or fat overlay. This presents a problem in calibrating for patients with other than average sized thyroids or heavy patients who have more than the average amount of fat tissue covering their thyroid gland.

SUMMARY OF THE INVENTION

It is thus an object of the invention to provide an animal body parts phantom, and in particular a thyroid phantom, which avoids the handling of radioactive liquids by laboratory personnel.

According to the invention, an animal body part phantom is provided comprising, a substrate sheet shaped in the form of an animal body part; a predetermined known amount of a radioactive tracer material substantially uniformly deposited on said substrate; and a tissue simulating material encapsulating and supporting said substrate.

BRIEF DESCRIPTION OF THE ACCOMPANYING DRAWINGS

DETAILED DESCRIPTION OF THE PREFERRED EMBODIMENTS

Figure 1:
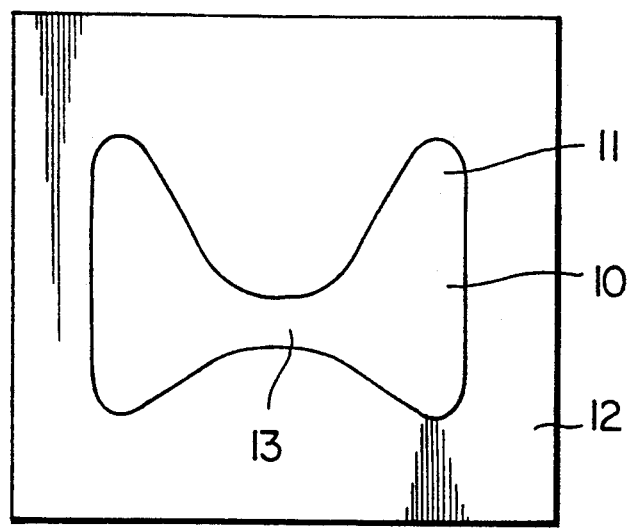
FIG. 1 is a plan view of the substrate in the form of a thyroid.

As seen in FIG. 1, the outline of the substrate 10 is first traced on a sheet of suitable material using a template 12. Specifically, the substrate sheet is cut to the shape of the thyroid, including two lobes 11 joined by an isthmus 13. i.e. the characteristic butterfly shape and size of the average thyroid is involved. Different sized thyroid shapes are also contemplated. Suitable materials include those which will absorb or adsorb the radioactive tracer. Liquid absorbent cellulosic-based materials such as paper and cardboard have been found to be most suitable. Suitable adsorbent materials include synthetic resins such as polyethylene. A preferred paper material is the highly liquid absorbent Whatman ® No. 541 fast filter paper. Excess handling of the paper should be avoided to prevent oily deposits that could impede absorption of radioactive solutions.

Figure 2:
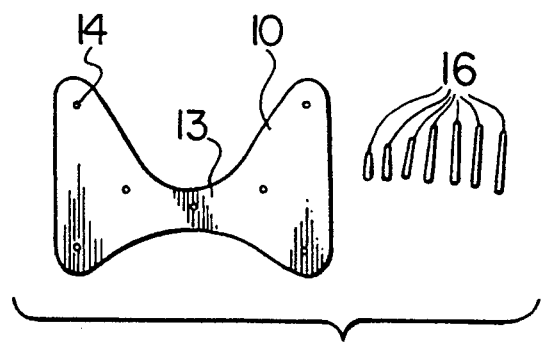
FIG. 2 is a plan view of the substrate illustrating the spacer pins and their location on the substrate.

As seen in FIG. 2, holes 14 are punched in the paper substrate 10. Spacer pins 16 are inserted half way through the holes and glued in place, to position the paper as will be apparent hereinafter. Wooden toothpicks cut to the appropriate lengths have been found acceptable for this purpose.

The paper substrate is then placed in a Petri dish and spiked with a predetermined known amount of radioactive tracer material i.e. $^{125}$I or $^{131}$I in standard solutions in water. As will be apparent hereinafter, a known amount of the radioactive material is required to provide a specific activity of tracer material in the phantom. Both of these radio-isotopes are used to permit calibration at different energy levels i.e. $^{125}$I emits photons around 30 KeV whereas $^{131}$I emits at about 364.5 KeV. The former is typically used in research applications and the latter for medical purposes. Since the half-lifes of these isotopes are relatively short, simulants may be used. In the case of the former, $^{129}$I is often employed. For the latter, a mixture of $^{133}$Ba and $^{137}$Cs is used. The shelf-life of these simulants is considerably longer. The use of simulants thus extends the useful life of the device. The paper substrate absorbs the radioactive solution. As a result, the radio-iodine is substantially distributed in the paper substrate. Thorough drying is then effected under a heat lamp to completely eliminate any moisture. Otherwise, any remaining water could chemically react with the encapsulating material. Adsorbent substrates must be kept in a horizontal position during the drying step to optimize the distribution of radio-iodine.

Figure 3:
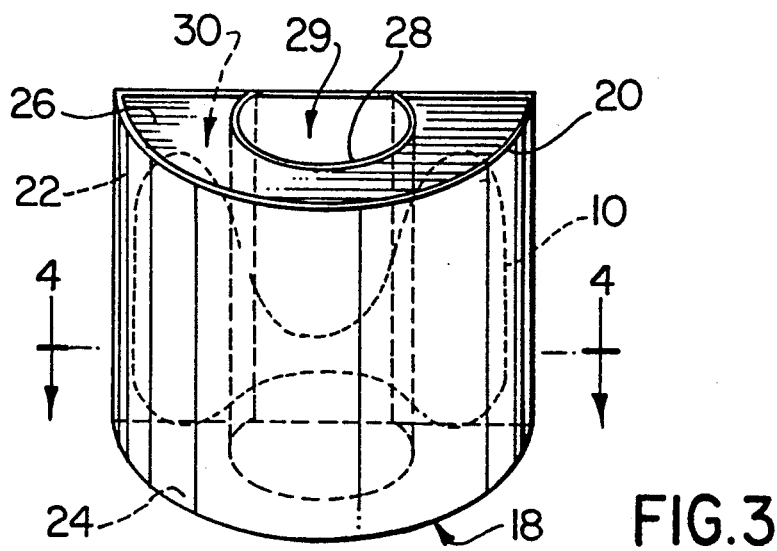
FIG. 3 is a schematic representation, partly in section, of the container, illustrating the location of the substrate.

Turning to FIG. 3, the outer container 18 for enclosing the thyroid phantom is illustrated. It is seen that the container is generally in the shape of a section of a cylinder, defined by a convex front wall 20, a flat rear wall 22, and a semi-circular bottom 24, and top 26 portions. A convex wall section 28 is provided centrally (but not concentrically with the front wall) and adjacent to the rear wall 22. The rear wall 22 is typically 68 mm in height. The depth at the centre of the top 26 and bottom portions 24 is 30 mm. The convex front wall and the convex centre wall are cut from 69.85×3.2 mm and 25.4×3.2 mm tubing material, respectively, and the other portions from 3 mm sheet material and adhesively attached with 3M CA-5 glue. The material used is typically an acrylic resin material. Such materials are sold under the Trademarks Plexiglas and Lucite.

Respecting the inner construction of the container, the central convex wall 28 includes an empty cavity 29 which simulates the location of the trachea and esophagus. A frontal cavity 30 is provided for location and positioning of the paper substrate. The frontal cavity 30 is defined by the convex wall 28 and front convex wall 20. It will be apparent that the frontal cavity is wider adjacent to the rear wall 22. This is to approximate the shape "in plan" of an actual thyroid. The paper substrate 10 is thus seen to be vertically positioned, with the isthmus 13 closer to the bottom, in the frontal cavity 30 substantially equidistant from the front wall 20 and the central wall 28. Location in this manner is achieved by means of the aforementioned spacer pins 16. The idea is that by positioning the radioactive substrate 10 inside the container 18 equidistance from the walls, one would most closely mimic the homogeneously distributed radioactivity in the actual thyroid gland.

Figure 4:
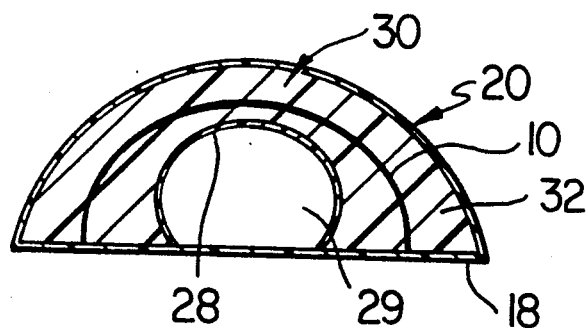
FIG. 4 is a plan view of the container partly in section, taken along the line 4—4 in FIG. 3, illustrating the location of the paper substrate and the supporting material.

Referring to FIG. 4, it is seen that the paper substrate 10 presents a convex curved configuration which generally follows the contour of the front convex wall 20. In operation it is this view which faces the radiation detecting equipment to effectively simulate the real homogeneous distribution of radioactive material in a thyroid. The supporting tissue simulating material 32 is pour cast to encapsulate and completely fill the front cavity 30 which acts as a mold. In this manner, support and protection (e.g. from mechanical shock) of the paper substrate are effected.

In order to effectively simulate human tissue, the average density (1.07 g/cm$^3$) and radiological properties (mass attenuation coefficient) of the tissues are substantially matched. The typical amount of adipose tissue covering the thyroid in the body is also considered i.e. about 1 cm.

One useful tissue simulating material is Scotchcast ® Electrical Resin 226, a rubbery castor-based polyurethane liquid resin available from 3M of St. Paul, Minn. For example, its density (1.06 g/cm$^3$), exotherm, low cure shrinkage, low viscosity, low volatility at room temperature and room temperature curing properties are suited for this application.

Other synthetic resin materials with similar properties could also be used, for example, the prior art RSD phantom uses Adiprene which is a trademark for a four-part polyether based urethane pre-polymer available from Uniroyal Chemical.

The Scotchcast resin is a two-part system i.e. Parts A and B. Part A contains a polyisocyanate and diphenyl methane diisocyanate. The mixing proportion are 2 parts of component A to 5 parts of component B. The mixture of Parts A and B is poured into the frontal cavity 30 to fill the cavity and cured at room temperature overnight. The top portion 26 is then glued in place.

It will be appreciated that the container is essential to the invention. It is contemplated that once molded in the container, the container could be discarded and the phantom used on its own. However, it is preferable to use the container to protect the phantom and facilitate mounting in a neck phantom as described below.

Figure 6:
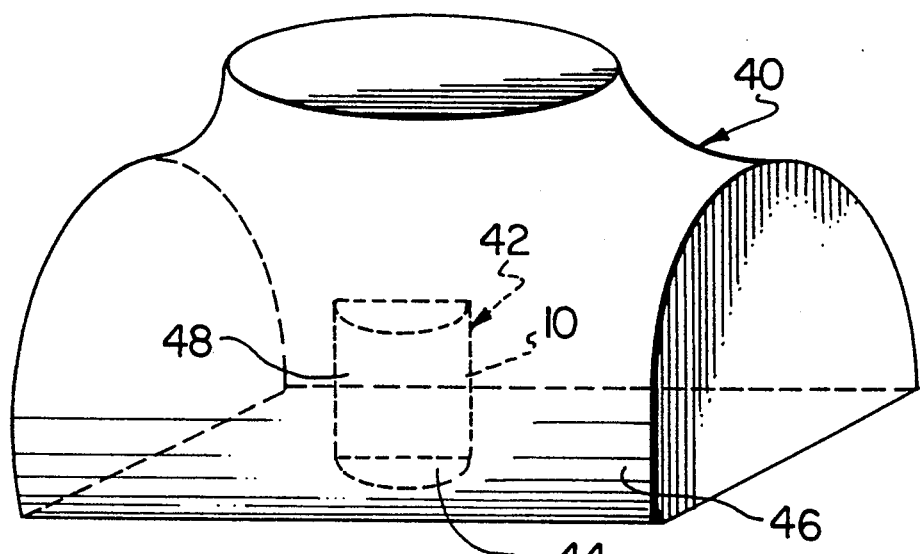
FIG. 6 is a schematic representation, partly in section of a neck phantom, illustrating the location of the thyroid phantom in use.

Turning to FIG. 6, a solid neck phantom 40 constructed from a mold of a Rando (trademark) body phantom is illustrated. The neck phantom is conveniently made of the same Scotchcast 226 polyurethane resin. A central cavity 42 is provided for receiving the thyroid phantom. The cavity 42 is accessed through an opening 44 provided in the base 46 of the neck phantom.

The cavity 42 is of the same general shape and size of the container 18 and includes a front convex portion 48 of the same contour as the front surface section 20 of the container.

Figure 7:
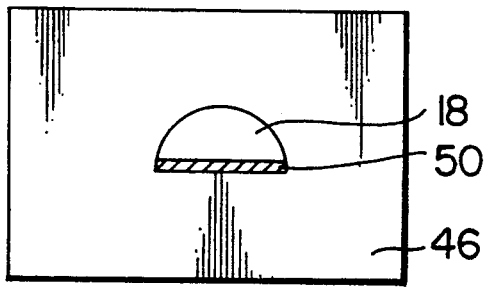
FIG. 7 is a bottom view of a neck phantom illustrating the retainer.

As best seen in FIG. 7, a synthetic resin material retainer block 50 preferably made from Scotchcast 226, placed behind the container is used to ensure a snug fit of the container 18 in the cavity with the front wall 20 contacting the front wall 48 of the cavity. The container can accommodate substrates of different sizes to simulate different sized thyroids.

Figure 8:
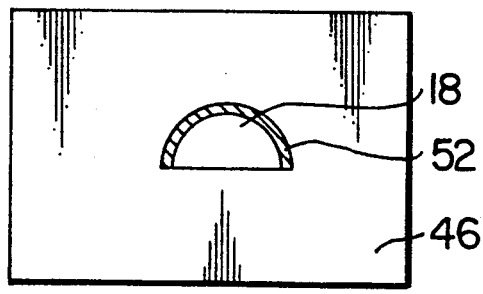
FIG. 8 is a bottom view of a neck phantom illustrating the fat simulating overlay.

Moreover, in some cases involving heavy patients, a thicker than 1 cm layer of adipose tissue is likely to be present. To best simulate such conditions, an additional overlay of acrylic plastics material may be included. For example, using the same 3.2 mm (wall thickness) acrylic tubing, a frontal overlay may be constructed. As seen in FIG. 8, a convex frontal overlay 52 is located in front of and in contact with the front section 20 of the container. In this case a retainer is not required. It has been determined that a 6.4 mm thick overlay (e.g. composed of two convex pieces of tubing one 76.2 mm of OD×3.2 mm W and the other 82.6 mm OD×3.2 mm W) glued together i.e. 6.4 mm tubing effectively simulates 8 mm of adipose tissue. (This is the case because of the almost identical values of mass attenuation coefficient for adipose and acrylic.) The photons emitted by $^{125}$I and $^{129}$I have the average energy around 30 KeV whereas the main photon peak for the decaying $^{131}$I occurs at 364.5 KeV. The corresponding mass attenuation coefficients for adipose and acrylic are 0.0306 and 0.0303 m$^2$/kg for 30 KeV photons, and 0.0106 and 0.0103 m$^2$/kg for 400 KeV photons, respectively. In this manner a total of 18 mm of tissue is simulated. For both FIG. 7 and FIG. 8 embodiments, a semi-circular synthetic resin material lid, preferably made from Scothcast 226, is used to close the cavity to hold the container in place. It is important to note that any number of convex pieces of acrylic tubing (not just two) that fit inside each other can be used in combination with retainers of different thicknesses to create fat overlays of different thicknesses. The cavity size would have to be enlarged if thick overlays are desired. This enlarged cavity would be universal regardless of the patient. This would allow calibration for people with different amount of fat overlaying the thyroid.

It will be thus appreciated that the thyroid phantom according to the invention is easily adaptable to simulate different sizes of thyroids and different amounts of overlaying fat tissue without having to alter the neck phantom.

EXPERIMENTAL

It has been determined mathematically that for Scotchcast 226, a 7.2 mm thickness of front wall of the neck phantom plus the 3.2 mm thickness of acrylic container wall is effective. Specifically, for $^{125}$I (average peak photon energy ≃30 KeV)

$$X_{ad} = \frac{X_r}{1.172} \quad (1)$$

and for $^{131}$I (main peak photon energy 364. KeV≃400 KeV)

$$X_{ad} = \frac{X_r}{1.183} \quad (2)$$

The convex acrylic front wall of the container plus the neck phantom covering thickness of Scothcast 226, will simulate 1 cm of adipose tissue. For the purposes of this calculation, the thickness of supporting material covering the paper substrate maybe ignored in view of the positioning of the substrate as described above. It was determined that 7.2 mm of the resin plus 3.2 mm of the acrylic do just that.

At 30 KeV: calculations show that 3.2 mm of acrylic simulates 3.9 mm of adipose; 7.2 mm of Scotchcast 225 simulates according to (1):

$$\frac{7.2}{1.172} = 6.1 \text{ mm of adipose}$$

Total simulated adipose thickness is thus $$3.9 \text{ mm} + 6.1 \text{ mm} = 10.0 \text{ mm} = 1 \text{ cm}$$

At 364.5 KeV≃400 KeV: calculations show that 3.2 mm of acrylic simulates 3.8 mm of adipose; 7.2 mm of Scotchcast 226 simulates according to (2):

$$\frac{7.2}{1.183} = 6.1 \text{ mm of adipose}$$

The total simulated adipose thickness is thus:

$$3.8 \text{ mm} + 6.1 \text{ mm} = 9.9 \text{ mm} \simeq 1 \text{ cm}$$

It has also been determined mathematically (see FIG. 5) that the mass radiation attenuation coefficient of Scotchcast 226 is $2.34 \times 10^{-2}$ m²/kg at 30 KeV photon energy, characteristic of $^{125}$I.

Moreover, from the curve defined by circles (see FIG. 5) we see that the transmission of 30 KeV photons by a 1 cm thick slab of 3M Scotchcast 226 is 78%, i.e. 0.78. Transmission is defined by $$\frac{I}{I_o} = \exp(-\mu \rho \chi) \quad (3)$$

where:
- $I_o$—intensity of a bare radioactive source measured by a detector.
- $I$—intensity of the radioactive source attenuated by a 1 cm thick Scotchcast 226 slab (measured by the same detector)
- $\mu$—mass attenuation coefficient of Scotchcast 226.
- $\rho$—density of Scotchcast 226 (1.06 g/cm³)
- $\chi$—thickness of the slab (1 cm in this case)

Putting all the known quantities into equation #(3) we get:

$$0.78 = \exp(-\mu \times 1.06 \text{ g/cm}^3 \times 1 \text{ cm})$$

Now the above equation can be selected for $\mu$. This gives us the value for mass attenuation coefficient, $\mu$, of Scotchcast 226.

$$\mu = 0.234 \text{ cm}^2/\text{g} = 2.34 \times 10^{-2} \text{ m}^2/\text{kg}$$

The adiprene based material from which the RSD phantom is made has also been tested for transmission properties. This data is provided in FIG. 5 as well. It is denoted by diamonds (L.L.N.L. stands for Lawrence Livermore National Lab.—the place where the phantom was originally fabricated).

Figure 5:
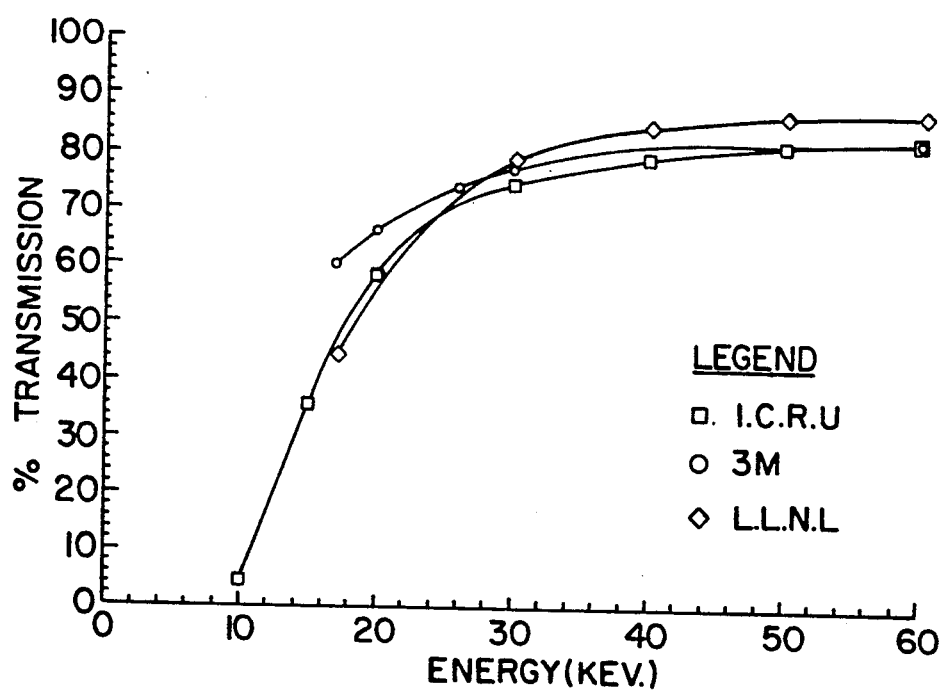
FIG. 5 is a graph illustrating the radiation attenuation of the supporting material.

Also shown in FIG. 5 are transmission values for adipose (squares) based on the data from the Report 44 of the International Commission on Radiation Units and Measurements (I.C.R.U.)

Similarly, the mass attenuation coefficient of Scotchcast 226 at phantom energy of 364.5 KeV has been determined to be:

$$\mu = 0.88 \times 10^{-2} \text{ m}^2/\text{kg}$$

(This calculation does not come from FIG. 5. It was calculated in another—but very similar experiment.)

A further experiment was conducted to compare the performance of the thyroid phantom according to the invention to two other commercially available thyroid phantoms. The results are tabulated in Table 1 below.

In the experiment, the other phantoms tested are identified as RSD and ANSI. The RSD phantom is the one described above in the Description of the Prior Art. The ANSI (American National Standards Institute) phantom is a rather crude device comprising a large solid cylindrical acrylic body having a cylindrical cavity which accommodates a sample bottle containing the radio-iodine held in an acrylic carrier.

Procedure

1. The three phantoms are prepared with the precisely known amounts of radio-iodine i.e. $^{125}$I and $^{131}$I or simulants therefore using commercially available standard solutions in water. For $^{125}$I, a simulant $^{129}$I, from Amersham Laboratories—Product Code 1SZ.44. For $^{131}$I, a simulant mixture of $^{133}$Ba and $^{137}$Cs in approximate ratio of 9.3:1 by activity, also from Amersham-Product Code 1Zy.55

2. Each phantom is then placed at the same precise distance from a radiation detector. (In this case, a Phoswich (trademark) Detector 15.2 cm diameter, containing NaI(Th) crystal 0.3 cm thick and CsI Crystal 5.1 cm thick, manufactured by Horsaw Co. Crystal and Electronics Products of Solon, Ohio.

3. The output signal (expressed as number of a radiation counts per second cps) is then measured for each phantom at various distances of phantom from detector.

The efficiency of the phantoms is then calculated according to the mathematical expression $$E = \frac{\text{cps}}{\text{activity}}$$

The uptake of radio-iodine by an actual thyroid will vary with the degree of exposure. It could be lower or higher than the activity deposited onto the paper substrate. What is important is that the activity deposited onto the substrate be known very precisely in order to be able to perform accurate calibration of radiation detecting equipment. In this case high and low activity thyroid standards were made (approximately 9200 Bq and 1500 Bq for $^{129}$I, and 4800 Bq and 1100 Bq for simulated $^{131}$I).

The amount of activity deposited is measured by weighing the "baby" bottle (pipette-like device containing the standard solution) before and after deposit. The deposited weight is then multiplied by the known activity per unit weight of the standard solution to obtain the total deposited activity as tabulated in table 1.

TABLE 1

| Distance between Phantom & detector | Efficiency RSD - cps/nCi | Efficiency BRMD - cps/nCi | Efficiency ANSI - cps/nCi |
|---|---|---|---|
| ON CONTACT | 5.730 | 6.100 | 6.791 |
|  | 5.603 | 5.757 | 7.088 |
|  | 5.883 | 5.860 | 6.855 |
|  | 5.956 | 5.860 | 6.968 |
|  | 5.728 | 5.919 | 6.870 |
| AVERAGE | 5.780 ± 0.062 | 5.899 ± 0.057 | 6.914 ± 0.052 |
| 18 CM | 0.837 | 0.764 | 0.790 |
|  | 0.837 | 0.768 | 0.792 |
|  | 0.801 | 0.787 | 0.786 |
|  | 0.823 | 0.781 | 0.784 |
|  | 0.824 | 0.780 | 0.787 |
| AVERAGE | 0.824 ± 0.007 | 0.776 ± 0.004 | 0.788 ± 0.001 |
| 30 CM | 0.341 | 0.331 | 0.322 |
|  | 0.331 | 0.332 | 0.329 |
|  | 0.334 | 0.325 | 0.319 |
|  | 0.332 | 0.326 | 0.330 |
|  | 0.337 | 0.333 | 0.322 |
| AVERAGE | 0.335 ± 0.002 | 0.329 ± 0.002 | 0.324 ± 0.002 | nCi is the abbreviation for nano-Curie = $10^{-9}$ Ci. 1nCi = 37 Bq (Becquerel).

It will be seen from table 1 that the efficiency results for all three phantoms are fairly close at each distance from the detector, (mostly within 2-3 standard deviations) and essentially the same at 30 cm from the detector. Accordingly, the phantom according to the invention works equally as well as the conventional phantoms but avoids the various drawbacks of these devices as discussed above.

It will be appreciated by those skilled in the art of that while the invention has been described in relation to a thyroid phantom, it is also applicable to other animal body parts phantoms. Specifically, this technique of simulating the incorporation of radioactivity into tissue could easily be applied to other organs or body parts. For example, radionuclides of Pu, Co, Th, etc. tend to accumulate in the bones and the liver. A hollow shell could be fabricated in the shape of the liver. A substrate spiked with a radioactive tracer could then be inserted inside the hollow shell (liver in this case). The substrate could be, for example, attached with glue to the walls of the shell. The hollow shell can then be filled with tissue simulating material (such as Scotchcast 226 for example). Similarly, contaminated bone could be simulated with a bone phantom. To simulate radio-activity deposited into ribs (for example), a hollow rib phantom could be fabricated and a radioactive substrate inserted therein. The hollow rib phantom would then be filled with tissue simulating material.

Another way to simulate contaminated bones would be to wrap radioactive substrate around parts of the real skeleton and attach with glue. Those parts could then be inserted inside a mold. The mold will then be filled with tissue simulating material.

We claim:

1. An animal body parts phantom, comprising:
   a substrate sheet, shaped in the form of an animal body part;
   a predetermined known amount of a radio-active tracer material substantially uniformly deposited on said substrate; and
   a tissue simulating material encapsulating and supporting said substrate.

2. A phantom according to claim 1, wherein the radio-active tracer material is selected from $^{125}$I, $^{131}$I, $^{129}$I, a mixture of $^{133}$Ba and $^{137}$Cs, and radio nuclides of Pu, Co and Th.

3. A phantom according to claim 2, wherein the tissue stimulating material is a polyurethane material.

4. A phantom according to claim 3, wherein the animal body parts are selected from the thyroid, the liver and bones.

5. A thyroid phantom comprising:
   a substrate sheet, shaped in the form of a thyroid;
   a predetermined known amount of radio-active tracer material substantially uniformly deposited on said substrate; and
   a tissue simulating material encapsulating and supporting said substrate.

6. A thyroid phantom according to claim 5, including a snug fitting outer container enclosing said encapsulated substrate.

7. A thyroid phantom according to claim 6, wherein the outer container includes a cavity, having convex frontal and rear walls, the substrate being vertically positioned in said cavity by spacer pins to locate said substrate substantially equidistant from said frontal and rear walls.

8. A thyroid phantom according to claim 7, wherein said tissue simulating material is pour cast into said cavity, which acts as a mold for said material, to encapsulate said substrate.

9. A thyroid phantom according to claim 8, in combination with a neck phantom, said neck phantom having a base and a central cavity of substantially the same shape as said container, said cavity being accessible through an opening in the base, and including a frontal overlay to simulate additional tissue covering an actual thyroid.

10. A thyroid phantom according to claim 8, in combination with a neck phantom, said neck phantom having a base and a central cavity of substantially the same shape as said container, said cavity being accessible through an opening in the base, and including a retainer block to ensure a snug fit of the container in the cavity.

11. A thyroid phantom according to claim 10, wherein the neck phantom covering the container, together with the frontal wall simulates the about 1 cm tissue thickness covering an actual thyroid.

12. A thyroid phantom according to claim 8, wherein the tissue simulating material has a density and mass attenuation coefficient substantially matching those of human tissue.

13. A thyroid phantom, according to claim 12, wherein the tissue simulating material is a rubbery polyurethane material.

14. A thyroid phantom according to claim 12, wherein the substrate is a cellulosic material.

15. A thyroid phantom according to claim 14, wherein the cellulosic material is a highly liquid absorbent paper material.

16. A thyroid phantom according to claim 15, wherein the radioactive tracer is radioactive iodine.

17. A thyroid phantom according to claim 15, wherein the radioactive tracer is selected from $^{125}$I, $^{131}$I, $^{129}$I and a mixture of $^{133}$Ba and $^{137}$Cs, in a water solution.

18. A thyroid phantom according to claim 17, including a convex overlay contacting the frontal wall of the container to simulate the presence of additional tissue covering an actual thyroid.

19. A thyroid phantom according to claim 18, wherein the container and overlay are made of an acrylic resin material.

* * * * *